US005650394A

United States Patent [19]
Terao et al.

[11] Patent Number: 5,650,394
[45] Date of Patent: Jul. 22, 1997

[54] USE OF URINASTATIN-LIKE COMPOUNDS TO PREVENT PREMATURE DELIVERY

[75] Inventors: Toshihiko Terao; Naohiro Kanayama, both of Shizuoka, Japan; David Casal, Foster City, Calif.

[73] Assignee: Adeza Biomedical, Sunnyvale, Calif.

[21] Appl. No.: 148,160

[22] Filed: Nov. 4, 1993

[51] Int. Cl.$^6$ .......................... A61K 38/00; G01N 33/53; G01N 33/537; G01N 33/543

[52] U.S. Cl. .................... 514/14; 514/2; 514/8; 514/21; 514/653; 514/24; 514/420; 514/61; 514/192; 514/195; 514/198; 514/29; 514/200; 514/209; 424/682; 424/709; 424/94.4; 435/7.1; 435/7.4; 435/7.9; 435/7.91; 435/7.92; 435/7.93; 435/7.94; 435/7.95

[58] Field of Search ..................... 514/2, 8, 14, 21, 514/653, 420, 24, 61, 192, 195, 198, 29, 200, 209; 424/682, 709, 94.4; 436/518, 63, 65, 814, 817, 818, 906; 435/7.1, 7.4, 7.9–7.95; 935/76, 81

[56] References Cited

U.S. PATENT DOCUMENTS 5,118,668  6/1992  Auerswald et al. ........... 514/12

FOREIGN PATENT DOCUMENTS

| 100985 | 8/1983 | European Pat. Off. . |
|---|---|---|
| 0300459 | 1/1989 | European Pat. Off. . |
| 401 508 | 5/1990 | European Pat. Off. . |
| 0486001 | 5/1992 | European Pat. Off. . |
| 543 240 | 5/1993 | European Pat. Off. . |
| 643075 | 2/1994 | European Pat. Off. . |
| 624 644 | 11/1994 | European Pat. Off. . |
| 5-308988 | 11/1993 | Japan . |
| WO 82/03011 | 9/1982 | WIPO . |
| WO95/12406 | 5/1995 | WIPO . |

OTHER PUBLICATIONS

Kanayama et al, ACTA Obstet. Gynaecol. Jpn. (Jpn. Ed.), vol. 40(7) pp. 917–918 1988.

Merck, 11th edition (1989) pp. 37, 305, 1402.

Copper et al., "A multicenter study of preterm birth weight and gestational age-specific neonatal mortality" *Am. J. Obstet. Gynecol.* (1993) 168(1):78–84.

Creasy, "Preterm birth prevention: Where are we?" *Am. J. Obstet. Gynecol.* (1993) 168(4):1223–1230.

Morrison et al., "Oncofetal fibronectin in patients with false labor as a predictor of preterm delivery" *Am. J. Obstet. Gynecol.* (1993) 168(2):538–542.

Pircon et al., "Controlled trial of hydration and bed rest versus bed rest alone in the evaluation of preterm uterine contractions" *Am. J. Obstet. Gynecol.* (1989) 161(3):775–779.

Morrison et al., "Preterm birth: A puzzle worth solving" *Obstet. Gynecol.* (1990) 76(Supplement 1):5S–12S..

Lockwood et al., "Fetal fibronectin in cervical and vaginal secretions as a predictor of preterm delivery" *N. Engl. J. Med.* (1991) 325(10):669–674.

McGregor et al., "Use of antibiotics for preterm premature rupture of membranes" *Obstet. Gynecol. Clin. North Amer.* (1992) 19(2):327–338.

Mercer et al., "Erythromycin therapy in preterm premature rupture of the membranes: A prospective, randomized trial of 220 patients" *Am. J. Obstet. Gynecol.* (1992) 166(3):794–802.

Kirschbaum, "Antibiotics in the treatment of preterm labor" *Am. J. Obstet. Gynecol.* (1993) 168(4):1239–1246.

Kanayama et al., "Effects of urinastatin vaginal suppositories in patients with imminent premature delivery"–Translated from *Nihon Sanka Fujinka Gakkai zasshi/Acta Obstet. Gynaecol. Jpn.* (1992) 44(4):110–115.

Fuzishiro et al., "A case of threatened premature labor with formation of bag of the membrane that could be maintained up to 36 weeks of gestation" *Japan J. Obstet. Gynecol. Neonatl. Hematol.* (1992) 2:107–110. An english abstract can be found on page 1 of this publication.

Inaba et al., "Effect of urinastatin on disseminated intravascular coagulation" *Folia pharmacol. japon.* (1986) 88:239–244. An English abstract is also enclosed herewith.

Terao et al., "Preterm PROM" *Sanfujinka Jissai* (1988) 37(2):159–168. An English abstract is also enclosed herewith.

Merrifield, "Solid phase peptide synthesis: I. The synthesis of a tetrapeptide" *J. Am. Chem. Soc.* (1963) 85:2149–2154.

Proksch et al., "The purification of the trypsin inhibitor from human pregnancy urine" *J. Clin. Lab. Med.* (1972) 79(3):491–499.

Kassell, "Bovine trypsin–kallikrein inhibitor (Kunitz inhibitor, basic pancreatic trypsin inhibitor, polyvalent inhibitor from bovine organs)" *Meth. Enzymol.* (1970) 19:844–852.

English abstract of Kanayama et al., "Effects of granulocyte elastase inhibitor (urinastatin) vaginal suppository on patients with imminent premature delivery" *Acta. Obstet. Gynecol. Japan* (1992) 44(4):477–482.

(List continued on next page.)

*Primary Examiner*—Toni R. Schneiner
*Assistant Examiner*—Sheela J. Huff
*Attorney, Agent, or Firm*—Townsend and Townsend and Crew LLP

[57] ABSTRACT

The present invention provides a method of diagnosing and treating a pregnant female at risk for impending preterm delivery. The method comprises the step of diagnosing imminent preterm delivery by testing with a method that has a sensitivity of at least 80% and a specificity of at least 80%, or by testing for fetal fibronectin in the female's vaginal or cervical secretions. If imminent preterm delivery is indicated by the test, the next step comprises administering to the female a combination of a tocolytic agent, at least one urinastatin-like compound, and at least one antibiotic. Also provided is a pharmaceutical composition of MGMTSRY-FYNGTSMA (SEQ ID NO:1), RAFIQLWAFDAVKGK (SEQ ID NO:2) and an antibiotic.

15 Claims, 1 Drawing Sheet

OTHER PUBLICATIONS

English abstract of Fuzihiro et al., "A case of threatened premature labor with formation of bag of the membrane that could be maintained up to 36 weeks of gestation" *Case Report from Dept. of Obs. & Gyn.,Hamamatsu Univ. Sch. of Med.* p. 107.

English abstract of Ghoda et al., "Mechanism of the anti–osteoarthritic action of ulinastatin in comparison with those of indomethacin and triamcinolone" *Folia pharmacol. japon* (1992) 99:93–107.

English abstract of Kato et al., "Effects of ulinastatin on experimental arthritis" *Folia pharmacol. japon* (1988) 91:29–40.

English abstract of Ohnishi et al., "Therapeutic effects of human urinary trypsin inhibitor on acute experimental pancreatitis" *Folia pharmacol. japon* (1983) 81:235–244.

English abstract of Shibutani et al., "Preventive effects of urinastatin on tissue degradation" *Fuji Central Research Laboratory, Mochida Pharmaceutical Company., Ltd.* 1 page total.

English abstract of Ohnishi et al., "Effects of human urinary trypsin inhibitor against operative stress" *Folia pharmacol. japon* (1983) 85:1–6.

English abstract of Fukutake, "In vitro observations on antithrombotic action of urinastatin" *Folia pharmacol. japon* (1987) 90:163–169.

English abstract of Sato, "Effects of urinastatin on energy metabolism disorder during shock" *Folia pharmacol. japon* (1986) 88:195–203.

English abstract of Inaba, "Mode of action of urinastatin, human urinary trypsin inhibitor, on adrenocorticotropic hormone" *Fuji Central Research Laboratory, Mochida Pharmaceutical Company., Ltd.* 2 pages total.

English abstract of Ohzawa et al., "Pharmacokinetic study of ulinastatin after intra–articular administration to rabbits" *J. Pharmacobio–Dyn.* (1991) 14:s–37.

English abstract of Ohzawa, "Studies on the metabolic fate of ulinastatin (1): Pharmacokinetics in rats, mice and rabbits following a single intravenous dose" *Fuji Central Research Laboratory, Mochida Pharmaceutical Company., Ltd.* 1 page total.

English abstract of (author not identified) "Mechanism of action of ulinastatin on multiple organ failure–Its effects on leukocytes" *Biotherapy* (1992) 6(3):263–264.

English abstract of Inaba, "Effect of urinastatin on disseminated intravascular coagulation" *Folia pharmacol. japon.* (1986) 88:239–244.

Kato et al., "Effect of human urinary trypsin inhibitor (ulinastatin) on arthritis in rabbits induced by hyperimmunization with heat–killed *Escherichia coli*" *Fuji Central Research Laboratory, Mochida Pharmaceutical Company., Ltd.* 9 pages total.

Ohnishi et al., "Effects of urinary trypsin inhibitor on pancreatic enzymes and experimental acute pancreatitis" *Dig. Dis. and Sci.* (1984) 29(1):26–32.

Ohnishi et al., "Pharmacological activities of a trypsin inhibitor, urinastatin" translated from *Oyo Yakuri* 31 (1986) 31(3):663–675.

Takeda et al., "The effect of ulinastatin and PVP–iodine for preventing premature rupture of the membranes" *J. Perinat. Med.* (1991) 19(Suppl. 2):247.

Nishijima et al., "Transvaginal ultrasonographic measurement of cervical length to predict certical incompetence and preterm delivery" *J. Perinat. Med.* (1991) 19(Suppl.2):247.

Iams et al., "Symptoms that precede preterm labor and preterm premature rupture of the membranes" *Am. J. Obstet. Gynecol.* (1990) 162(2):486–490.

Copper et al., "Warning symptoms, uterine contractions, and cervical examination findings in women at risk of preterm delivery" *Am. J. Obstet. Gynecol.* (1990) 162(3):748–754.

Rozeboom et al., "Relationship of admissions for false labor to perinatal outcome" *J. Repro. Med.* (1989) 34(4):285–288.

Katz et al., "Early signs and symptoms of preterm labor" *Am. J. Obstet. Gynecol.* (1990) 162(5):1150–1153.

Turnbull, "The early diagnosis of impending premature labour" *Eur. J. Obstet. Gynecol. Repro. Biol.* (1989) 33:11–24.

Kragt et al., "How accurate is a woman's diagnosis of threatened preterm delivery?" *Eur. J. Obstet. Gynaecol.* (1990) 97:317–323.

ACOG Technical Bulletin, "Preterm Labor" (1989) 133:1–6.

Kanayama et al., "*Kunitz–Type Trypsin Inhibitor Prevents LPS–Induced Increase of Cytosolic Free $Ca^{2}$+ in Human Neutrophils and Huvec Cells*" Biochem. & Piophys. 1995 pp. 324–330.

U.S. application No. 08/394,318, Terao et al., filed Feb. 1995.

Kanayama, et al., "Implication In Measurement of Granulocyte Elastase Activity of Cervical Mucus – A Sensitive Marker for Premature Delivery", *Int. J. Gynecol. Obstet.*, (Abstract Only) (1991) p. 60 (Abstract No. 0239).

Kanayama, et al., "Urinary Trypsin Inhibitor Suppresses Premature Cervical Ripening", *European Journal of Obstetrics and Gynecology and Reproductive Biology*, 60(2):181–186 (1995).

Kanayama, et al., "Intrauterine Defensive Mechanism of Amniotic Fluid and Fetal Membranes", *ACTA Obstet. Gynaecol. Jpn. (Jpn. Ed.)*, 46(8):673–765, (1994) English Abstract only.

FIGURE 1

| | Grp 1<br>n=66 | Grp 2<br>n=14 | Grp 3<br>n=33 | Grp 2&3<br>n=47 | Grp 4<br>n=25 | Grp 5<br>n=30 | All<br>(n=168) |
|---|---|---|---|---|---|---|---|
| Maternal Age (yr) | 26.7±5.0 | 26.7±4.0 | 28.4±6.1 | 27.9±5.6 | 27.0±5.0 | 27.7±4.9 | 27.2±5.2 |
| Parity n(%)<br>0<br>1<br>2<br>>2 | 27(40.9)<br>24(36.4)<br>10(15.2)<br>5(7.6) | 7(50.0)<br>3(21.4)<br>3(21.4)<br>1(7.1) | 11(33.3)<br>13(39.4)<br>5(15.2)<br>3(9.1) | 18(38.3)<br>16(39.4)<br>8(17.0)<br>4(8.5) | 11(44.0)<br>6(24.0)<br>5(20.0)<br>3(12.0) | 13(43.3)<br>12(40.0)<br>2(6.7)<br>3(10.0) | 69(41.1)<br>58(34.5)<br>26(15.5)<br>15(8.9) |
| EGA Toco (weeks) | 29.5±3.4 | 30.1±3.2 | 28.4±3.4 | 28.9±3.4 | 29.2±3.4 | 28.3±3.0 | 29.1±3.4 |
| Toco Index n(%)<br>2<br>3<br>4<br>5<br>≥6 | 15(22.7)<br>18(27.3)<br>17(25.8)<br>8(12.1)<br>8(12.1) | 4(28.6)<br>3(21.4)<br>4(28.6)<br>2(14.3)<br>1(7.1) | 9(27.3)<br>11(33.3)<br>5(15.2)<br>4(12.1)<br>4(12.1) | 13(27.7)<br>14(29.8)<br>9(19.1)<br>6(12.8)<br>5(10.6) | 6(24.0)<br>8(32.0)<br>7(28.0)<br>2(8.0)<br>2(8.0) | 8(26.7)<br>7(23.3)<br>8(26.7)<br>2(6.7)<br>5(16.7) | 42(25.0)<br>47(28.0)<br>41(24.4)<br>18(10.7)<br>20(11.9) |
| Elastase (mg/ml) | 2.1±1.5 | 2.4±1.3 | 2.2±1.6 | 2.2±1.5 | 2.1±1.3 | 2.0±1.5 | 2.1±1.5 |
| Hours to Neg UA | 1.4±1.4 | 4.9±3.3 | 5.7±6.0 | 5.5±5.3 | 1.8±2.0 | 3.1±3.4 | 3.1±3.9 |
| Recur UA n(%) | 21(31.8) | 1(7.1) | 4(12.1) | 5(10.6) | 4(16.0) | 2(6.7) | 32(19.0) |
| EGA Del (wks) | 36.1±3.4 | 38.2±1.3 | 36.9±3.1 | 37.3±2.8 | 37.4±2.7 | 37.3±3.2 | 36.8±3.2 |
| Interval (wks) | 6.5±4.1 | 8.1±3.8 | 8.5±4.3 | 8.4±4.2 | 8.2±4.4 | 9.0±3.5 | 7.7±4.2 |
| PTD <37 Wks n(%) | 28(42.4) | 1(7.1) | 7(21.2) | 8(17.0) | 5(20.0) | 3(10.0) | 44(26.2) |
| PTD <34 Wks n(%) | 14(21.2) | 0(0.0) | 5(15.1) | 5(10.6) | 2(8.0) | 2(6.7) | 23(13.7) |

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( x i ) SEQUENCE DESCRIPTION: SEQ ID NO:1:

| Met | Gly | Met | Thr | Ser | Arg | Tyr | Phe | Tyr | Asn | Gly | Thr | Ser | Met | Ala |
|---|---|---|---|---|---|---|---|---|---|---|---|---|---|---|
| 1 | | | | 5 | | | | | 10 | | | | | 15 |

( 2 ) INFORMATION FOR SEQ ID NO:2:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( x i ) SEQUENCE DESCRIPTION: SEQ ID NO:2:

| Arg | Ala | Phe | Ile | Gln | Leu | Trp | Ala | Phe | Asp | Ala | Val | Lys | Gly | Lys |
|---|---|---|---|---|---|---|---|---|---|---|---|---|---|---|
| 1 | | | | 5 | | | | | 10 | | | | | 15 |

.# USE OF URINASTATIN-LIKE COMPOUNDS TO PREVENT PREMATURE DELIVERY

FIELD OF USE

This invention relates to the diagnosis and treatment of pregnant females at risk for preterm delivery. This invention is a method of diagnosing females at risk for preterm delivery and of treating such females with a combination of a tocolytic, a urinastatin-like compound, and an antibiotic.

BACKGROUND

In spite of the advances in health care and particularly perinatology, the preterm delivery of babies continues to be a major public health problem because of its association with infant morbidity and mortality. For example, the results of a multicenter trial spanning several years of experience showed that infants born prematurely, i.e., between 20 and 36 weeks gestation, accounted for 9.6% of births (Copper et al. *Amer. J. Obstet. Gynecol.* 168: 78, 1993). In that study, 83% of infant deaths occurred in gestations delivering prior to 37 weeks, and 66% involved gestations of less than 29 weeks.

Serious neonatal complications also decrease as the period of gestation increases. The incidence of neonatal respiratory distress syndrome decreases markedly after 36 weeks of gestation. Likewise, the incidence of neonatal patent ductus arteriosus and necrotizing enterocolitis decreases markedly after 32 weeks of gestation. According to Creasy, "high grade intraventricular hemorrhage diminishes rapidly after 27 weeks and is virtually absent after 32 weeks" (Creasy, *Amer. J. Obstet. Gynecol.* 168: 1223, 1993). Thus, extending the length of pregnancy beyond 32 weeks and preferable beyond 36 weeks could reduce the incidence of neonatal morbidity and virtually eliminate major causes of neonatal mortality.

According to Creasy, the incidence of preterm delivery in the United States is rising. When preterm delivery is defined as births occurring before 37 weeks of gestation, the incidence has risen from 9.4% in 1981 to 10.7% in 1989, accounting for approximately 425,000 of the 4,000,000 annual births in the United States of America.

There are several problems related to the rising incidence of preterm delivery in the United States. One problem is that physicians are unable to accurately predict which pregnancies are at risk. Factors known to be associated with elevated chronic risk of preterm delivery in otherwise asymptomatic women are low maternal socioeconomic status, lack of prenatal care, illicit drug use during pregnancy, previous preterm delivery, assisted reproductive techniques used in the current pregnancy (such as in vitro fertilization or gamete intra-fallopian transfer), smoking, uterine anomalies, and stress. (Morrison, *Amer. J. Obstet. Gynecol.* 168:538, 1993; Creasy, *Amer. J. Obstet. Gynecol.* 168:1223, 1993). Unfortunately, the majority of preterm births cannot be related to obvious causes, and even known causes may not necessarily be detectable or correctable. In fact, approximately one half of all preterm births occur in women who are pregnant for the first time and have no known risk factors for preterm delivery.

Even when women complain of symptoms frequently associated with acute risk of preterm delivery, it is often difficult to distinguish harmless symptoms from those associated with imminent prematurity. Many symptoms such as uterine contractions, change in vaginal discharge, abdominal discomfort, pelvic heaviness or change in cervical dimensions (effacement and dilatation) may harmlessly occur as normal variants in some pregnancies, while similar symptoms in other pregnancies can be associated with impending preterm delivery.

The majority of pregnant women who seek unscheduled emergency obstetrical care have complaints of excessive or painful uterine contractions of the uterus. Another frequent complaint is a tightening or pressure sensation which can indicate Braxton Hicks contractions of the uterus. Thus, physicians are often faced with the diagnostic dilemma of differentiating "true" from "false" labor with clinical information of limited diagnostic value. (Pircon et al., *Amer. J. Obstet. Gynecol.* 161:775, 1989) Copper et al. attempted to diagnose preterm labor using uterine activity (4 contractions/20 minutes or 8 contractions/60 minutes) coupled "with at least one of the following: ruptured membranes, cervical changes, cervical dilatation $\geq 2.0$ cm, or cervical length $\leq 1.0$ cm." Copper reported that this assessment was complicated by the fact that "contractions, regardless of the measure of frequency," normally increase during pregnancy.

The presence of advanced cervical dilatation (or effacement) is clinically important for determining risk of delivery (Morrison, *Obstet. Gynecol.* 76 (Suppl. 1) 55, 1990). Many clinical studies have demonstrated that cervical dilatation of greater than 3 cm is frequently associated with imminent delivery regardless of gestational age. Unfortunately, not all women with symptoms of threatened preterm delivery who ultimately deliver prematurely have advanced cervical dilatation when they present for emergency obstetrical care (Lockwood, *N. Engl. J. Med.* 325:669, 1991). Moreover, among the many clinical symptoms and signs associated with preterm labor or delivery, cervical dilatation is not necessarily the first clinical change noted. Typically, women with preterm labor who ultimately deliver prematurely seek obstetrical care for non-specific symptoms such as uterine activity, change in vaginal discharge, or abdominal discomfort which frequently precede cervical dilatation. Given the poor predictive power of these clinical signs and symptoms, "clinicians do not have a good discriminator of false versus true labor", resulting in as many as 50% of patients with "false" labor delivering early (Morrison et al., *Amer. J. Obstet. Gynecol.* 168:538, 1993).

In contrast, a more potent method of diagnosing patients at risk for preterm delivery is emerging. The presence of fetal fibronectin in cervical or vaginal secretions has been shown to be an accurate predictor for preterm delivery in women with symptoms suggestive of threatened preterm delivery (Lockwood et al., ibid.). A control group of women with uncomplicated pregnancies who delivered at term rarely had cervicovaginal concentrations of fetal fibronectin greater than 50 ng/ml at weeks 21–37 of gestation. In contrast, approximately 94% of women with preterm rupture of amniotic membranes had significantly elevated fetal fibronectin concentrations. But more importantly, about 50% of women with intact amniotic membranes and preterm uterine contractions had elevated concentrations of fetal fibronectin and more than 80% of these women delivered prematurely. Conversely, greater than 80% of women with intact membranes who did not have detectable cervicovaginal fetal fibronectin delivered at term. Thus, fetal fibronectin was demonstrated to be both a sensitive and specific predictor of preterm delivery.

Not surprisingly, the lack of available specific and sensitive indicators of preterm delivery risk among symptomatic women limits the ability of physicians to appropriately treat women judged to be at risk. In addition, there is considerable controversy in the obstetrical community regarding the therapeutic efficacy of available treatment regimens. Of course, assessment of any treatment regimen is complicated by the fact that perhaps as many as half of women diagnosed with preterm labor may not have the disease.

Effective and judicious treatment of preterm labor, especially in earlier gestation, is critical to the development of the fetus. As discussed above, births after 32–34 weeks of gestation are associated with lower rates of neonatal mortality and severe neonatal morbidity. Thus, prolongation of pregnancy and subsequent reduction of preterm delivery rates might be expected to lower neonatal morbidity and mortality. Unfortunately, in spite of the fact that obstetricians have identified more women as candidates for preterm labor treatment (known as tocolysis) over the last decade, the incidence of preterm delivery has actually increased over the same time span (Creasy, *Amer. J. Obstet. Gynecol.* 168:1223, 1993). The fact that the preterm delivery rate has not improved over the past decade is due not only to the inability of physicians to accurately identify patients truly in need of treatment but also to the failure of commonly available tocolytic drugs to impede the progress of labor.

Numerous controlled, clinical trials have been conducted to evaluate the clinical merits of various treatment regimens including bedrest, hydration, antibiotics, beta-adrenergic agonists, prostaglandin inhibitors, and calcium antagonists. The cumulative experience of these trials has clearly shown that common strategies for tocolytic intervention do not reproducibly prevent preterm delivery although they may be modestly effective for prolongation of pregnancy. Unfortunately, modest gains do not necessarily translate into improved neonatal outcome. As Creasy has noted, "numerous trials of prophylactic beta-adrenergic tocolytic usage with relatively low doses of medication have also not shown benefit in either singleton or multiple gestation".

The role of infection in preterm labor and use of antibiotics has been studied extensively, particularly in the context of premature rupture of the membranes (PROM). For example, a controlled clinical trial of antibiotic treatment with the broad spectrum erythromycin and ampicillin was associated with prolongation of gestation compared to the absence of antibiotics (McGregor and French, *Obstet. Gynecol. Clin. North Amer.* 19:327–38, 1992). In contrast, a controlled study of prophylactic erythromycin therapy showed no decrease in the incidence of maternal or neonatal infectious morbidity; however, in patients "destined to have chorioamnionitis and oligohydramnios", pregnancy was significantly prolonged (Mercer et al., *Amer. J. Obstet. Gynecol.* 166:794, 1992).

Only four trials evaluating the effect of antibiotics in treatment of women with preterm labor and intact membrances have been conducted. "Three of the four groups report an apparent prolongation of pregnancy with antibiotic therapy without impact on aggregate birth weight or perinatal mortality of the resultant infants" (Kirschbaum, *Amer. J. Obstet. Gynecol.* 168:1239, 1993). The results of these trials are difficult to interpret due to the use of different antibiotics, different clinical criteria for diagnosis of preterm labor and small numbers.

More promising strategies for reducing the incidence of preterm birth and lowering rates of neonatal morbidity and mortality may involve use of combination therapies, i.e., simultaneously using multiple, independent drugs. Kanayama (*Nihon Sanka Fujinka Gakkai Zasshi.* 44:110–15, 1992) reported a clinical study of women who showed signs of impending premature delivery. None of the patients had PROM, all were between the 24th and 35th weeks of pregnancy, and all had a "tocolysis index of 3–4", which was described as "imminent premature delivery of an intermediate degree." The tocolysis index is a relative index of delivery risk in which various risk factors for preterm delivery including status of amniotic membranes (rupture versus intact membranes), presence or absence of vaginal bleeding, estimation of cervical dilatation, and frequency of uterine contractions are semi-quantitatively assessed and scored, as indicated below.

| | Tocolysis Index | | | |
|---|---|---|---|---|
| | 0 pts | 1 pt | 2 pts | 3 pts |
| Cervical Dilation | 0 cm | 1 cm | 2 cm | 3 cm |
| Vaginal Bleeding | none | — | spotting | bleeding |
| Ruptured Membranes | intact | — | — | rupture |
| Uterine Activity | none | irreg. | regular | — |

The final tocolysis score represents the sum of each factor's "score" and hypothetically correlates to risk for preterm delivery as well as potential for successful tocolytic treatment. A tocolysis score of less than 3 indicates minimal risk for preterm delivery (and high probability of tocolytic success) while increasingly higher scores are associated with greater risk for preterm delivery (and lower probability of successful tocolytic intervention). While the tocolysis index is a modestly accurate method for assessing crude risk, it is neither reproducible between physicians (inter-observer error) nor a consistent predictor among individuals.

Kanayama and co-workers evaluated the effect of four therapeutic strategies on preterm delivery rate as well as cervical expression of granulocyte elastase, a putative mediator of the labor process. The four therapeutic regimens evaluated included ritodrine infusion only (Group A), daily urinastatin vaginal suppositories (Group B), combination of ritodrine infusion and vaginal urinastatin suppositories (Group C), and combination of ritodrine infusion, vaginal urinastatin suppositories, and systemic antibiotic therapy (Group D). When patients were treated with urinastatin (groups B, C and D), the elastase in vaginal secretions decreased. The time required for the number of uterine contractions (UC) to decrease to less than 1 per 30 minutes was about an hour for groups A, C and D; whereas this same UC decrease took an average of about 6 hours in group B (urinastatin alone). When UC had been depressed for 4 days, therapy was discontinued. Approximately 60% of the patients in group A experienced a recurrence; whereas, only 11–17% of the other groups experienced recurrent UC. In group A, 25% of women had premature deliveries, compared to no premature deliveries for groups B and D (9 and 8 patients, respectively) and only $\frac{1}{14}$ in group C.

However, in the above studies, no subjects with PROM or with tocolytic scores over 4 were tested. The authors suggested that "in more advanced cases of imminent premature delivery, further studies will be needed, since it is believed that localized therapies alone are insufficient." Moreover, there was no difference between group C (ritodrine and urinastatin) and group D (ritodrine, urinastatin and antibiotic).

Fuzishiro et al. reported that a patient with history of habitual abortion was observed to have a protruding amniotic sac at 20 weeks of gestation. She was treated with vaginal antibiotics and urinastatin, tocolytics and bed rest. Her pregnancy was maintained up to 36 weeks. *Japan. J. Obstet. Gynecol. Neonatal. Hematol.* 2:107–10, 1992.

Urinastatin, whose use is described above, is purified from human urine. It has been reported to suppress IL-1β- induced reduction of proteoglycan synthesis, superoxide generation, and inhibit a variety of serine proteases, such as trypsin, α-chymotrypsin, plasmin, leukocyte elastase and leukocyte cathepsin G.

Because urinastatin inhibits many chemical mediators in inflammation, urinastatin has been evaluated as an anti-inflammatory drug. Hence, urinastatin has been proposed for use in a variety of conditions, such as pancreatitis, septic shock, operative stress, arthritis, thrombosis and preterm delivery. It also has been proposed for use in disseminated intravascular coagulation. Inaba et al., *Folia Pharmacol. Japon.* 88: 239, 1986.

What is needed is an effective method to prolong pregnancy, prevent preterm delivery and reduce rates of neonatal morbidity and mortality in women with clinical signs of preterm labor.

SUMMARY OF THE INVENTION

The present invention provides a method of diagnosing and treating pregnant females at risk for impending preterm delivery. The method includes first testing for the presence of a significant amount of fetal fibronectin in the subject's vaginal or cervical secretions, which indicates that the pregnant subject is at risk for impending preterm delivery. If a significant amount of fetal fibronectin is present, the subject is administered effective amounts of a tocolytic agent, at least one urinastatin-like compound and at least one antibiotic.

In another aspect of the present invention, the method of diagnosing and treating a pregnant female at risk for impending preterm delivery includes diagnosing by testing for the presence of a significant amount of fetal fibronectin in the female's vaginal or cervical secretions. Females in whom a significant amount of fetal fibronectin is found are administered an effective amount of a tocolytic agent for less than about one week, an effective amount of at least one urinastatin-like compound daily until 35 weeks and an effective amount of an antibiotic until the subject gives birth.

In another aspect of the present invention, the method of diagnosing and treating pregnant subjects at risk for preterm delivery includes diagnosing imminent preterm delivery by means of a diagnostic test with specificity greater than 80% and sensitivity in excess of 80%. Subjects in whom the diagnostic test indicates imminent preterm delivery are given effective amounts of a tocolytic agent, at least one urinastatin-like compound and at least one antibiotic.

In another aspect of the present invention, there is provided a method of increasing the interval a pregnant woman carries the fetus after having been diagnosed as being at risk for imminent premature delivery. This method comprises the steps of administering an effective amount of a tocolytic agent, administering an effective amount of at least one urinastatin-like compound, and administering an effective amount of at least one antibiotic.

In another aspect of this invention, the method of diagnosing and treating a pregnant female at imminent risk for preterm delivery calls for determining the concentration of elastase in the cervical and/or vaginal fluids. If the female has an abnormally high level of elastase, the female is administered a tocolytic agent, at least one urinastatin-like compound and at least one antibiotic.

In another aspect of this invention, there is provided the pharmaceutical composition comprising MGMTSRYFYNGTSMA, RAFIQLWAFDAVKGK and an antibiotic.

BRIEF DESCRIPTION OF DRAWING

FIG. 1 shows a tabular summary of the data for pregnant women undergoing treatment according to Example 2.

DETAILED DESCRIPTION OF THE INVENTION

The present invention is a method for diagnosing and treating a pregnant female with impending premature delivery.

Definitions

As used herein, the term a "urinastatin-like compound" includes but is not limited to urinastatin, analogs and fragments thereof. Urinastatin is a glycoprotein having an approximate molecular weight of less than about 67 kD in purified form. Urinastatin inhibits trypsin, elastase, granulocyte elastase, chymotrypsin, plasmin, hyaluronidase, amylase and creatine phosphokinase. In addition, urinastatin inhibits cytokine action and stabilizes lysosomal surfaces.

Urinastatin has been sequenced and described in EP publication No. 0 100 985, published 1 Aug. 1983, which is hereby incorporated by reference. "Analogs of urinastatin" include polypeptides with conservative substitutions or deletions of amino acids which do not change the configuration, enzymatic activity, or activity in subjects. The urinastatin analogs include glycosylated and nonglycosylated polypeptides, as well as polypeptides with other post-translational changes, such as glycosylation with different sugars, acetylation, etc.

The term "fragments of urinastatin" includes urinastatin analogs which are oligopeptide portions of the glycoprotein and which are active for the intended use. Active oligopeptides include at least two peptides: the elastase inhibitor, comprising urinastatin amino acids 36–50, or MGMTSRYFYNGTSMA (SEQ ID NO:1), and the plasmin/cytokine inhibitor, comprising urinastatin amino acids 92–106, or RAFIQLWAFDAVKGK (SEQ ID NO:2).

"An effective amount of urinastatin" means an amount which significantly delays impending preterm delivery. An effective amount is sufficient by itself to diminish the rate of uterine contractions to about 1 in 30 minutes, within about 6 hours. An effective amount also is sufficient to depress the level of elastase in vaginal or cervical secretions significantly or to the level seen in females with normal pregnancies. The effective amount of urinastatin is preferably between about 500 and 10,000 Units per day. Preferably, the amount of urinastatin administered is about 750 to 5,000 Units per day. Even more preferably, the amount of urinastatin administered is about 1,000 U/day.

"A tocolytic agent" is defined as a drug which is capable of suppressing uterine contractions. Examples of tocolytic agents include but are not limited to ritodrine, terbutaline, salbutamol (albuterol), nifedipine and indomethacin.

"An effective amount of a tocolytic agent" means that quantity sufficient to reduce the number of uterine contractions (UC) to about 1–2 in 30 minutes within not more than 3 hours.

As used herein, "an antibiotic" includes a compound capable of killing and/or stopping multiplication of microorganisms. The microorganisms which are of greatest concern in pregnant females are the natural flora of the vagina. The microorganisms which cause very serious infections in pregnant females include anaerobes. In general, unless an infection is present and the causative organism has been identified for treatment by a specific antibiotic, the present invention calls for the administration of a broad spectrum antibiotic. Examples of broad spectrum antibiotics include amoxicillin, ampicillin, erythromycin, azithromycin, and cephalosporins. Administration of more than one antibiotic and combinations of antibiotics are contemplated in the present invention. One such combination is UNASYN® ampicillin sodium/sulbactam sodium. Clindamycin is preferred as it is effective against anaerobes.

An effective amount of an antibiotic is that amount normally used to treat an infection. For example, the recommended dosage of UNASYN is 1.5 to 3.0 grams every six hours. The PHYSICIAN'S DESK REFERENCE, 47th ed., 1993, lists suitable antibiotics and recommended dosages.

"Preterm delivery" means childbirth before the fetus has reached about 36 completed (<37.0) weeks of gestation, as determined by patient history, ultrasound sizing, last menstrual period or other accepted methods.

"Impending or imminent preterm delivery" includes delivery of a fetus with a gestational age between 24 and 34 completed weeks which occurs within 7 to 10 days of the time of diagnosis of threatened preterm delivery or preterm labor. Impending preterm delivery needs to be identified, so that appropriate intervention can be undertaken to prevent premature delivery of a child whose immaturity contributes to mortality and morbidity. Impending preterm delivery is often associated with premature separation of the placenta and fetal membranes and/or premature uterine contractions.

Testing for a specific marker for impending preterm pregnancy includes all the usual methods for testing substances, including solid state chemistry, chromatography and specific antibody recognition techniques. Antibody recognition techniques include various sandwich antibody assays, using radio-, fluorescent- and enzyme-linked antibodies. In the ELISA test (enzyme-linked immunoassay), enzyme-linked antibodies are subsequently exposed to chemicals on which enzymatic action causes formation of colored substances and/or substances detectable at a particular wavelength.

"Fetal fibronectin" is a unique fibronectin, found in amniotic fluid, placental tissue extracts and malignant cell lines. Fetal fibronectin is distinguished by an epitope termed the "oncofetal domain." This oncofetal domain is recognizable by a specific monoclonal antibody, which is used in a highly specific and sensitive test for fetal fibronectin.

"Significant amounts of fetal fibronectin" are levels which are above the concentrations commonly observed in the cervical or vaginal secretions of females with normal pregnancies between 24 and 34 completed weeks of pregnancy. In general, fetal fibronectin concentrations greater than about 50 ng/ml, as determined by a sensitive enzyme-linked immunoassay, are considered significantly elevated. Low levels of fetal fibronectin, i.e., concentrations of less than about 50 ng/ml, are present in the cervical and vaginal secretions of females with normal, uncomplicated pregnancies between 24 and 34 completed weeks. Although fetal fibronectin may be elevated before 24 weeks of pregnancy, this elevation is due to the normal development and growth of the placenta and does not necessarily reflect poor pregnancy outcome, e.g., preterm delivery, etc. Between 24 and 34 completed weeks, concentrations of fetal fibronectin greater than about 50 ng/ml in cervical or vaginal secretions are associated with preterm delivery.

"Analytical sensitivity" refers to the least amount of analyte that can be statistically distinguished from zero. In the present context, "clinical sensitivity" refers to the proportion of women who deliver prematurely with elevated fetal fibronectin concentrations. Preferably, the method for identifying female subjects with impending preterm delivery has a clinical sensitivity of at least 80%.

"Analytical specificity" refers to the test's ability to report positive results due only to the presence of the desired analyte. Absence of "cross-reactivity" also refers to the same phenomena as "analytical specificity". In the present context, "clinical specificity" refers to the proportion of women with preterm deliveries in whom the fetal fibronectin concentration in cervical or vaginal secretions is greater than 50 ng/ml. Preferably, the method for identifying female subjects with impending preterm delivery has a clinical specificity of at least 80%.

"Subjects" are defined as humans and mammalian farm animals, sport animals and pets. Farm animals include, but are not limited to, cows, hogs and sheep. Sport animals include, but are not limited to, dogs and horses. The category pets includes, but is not limited to, cats and dogs.

GENERAL CONSIDERATIONS

The present invention provides that the treatment and diagnosis of the patient at risk for preterm delivery by a highly specific and sensitive method.

The invention provides a treatment method for impending preterm delivery. In some aspects of the invention, this method is preceded by a suitable test for preterm delivery (i.e., one with both specificity and sensitivity greater than 80%).

The treatment step comprises administration of three drugs: a tocolytic agent, a urinastatin-like drug and an antibiotic.

While not wishing to be bound by any particular theory, the inventors have observed that infection of the amniotic sac known as chorioamnionitis is a major contributor to preterm delivery. Clinical chorioamnionitis is diagnosed if the patient has leukocytosis ($\geq$10,000 white blood cells/mm$^3$) and the maternal temperature is above about 100.4° F. and no other source of fever is found. A cervical culture may not be positive. After delivery, the placental membranes can be seen to have polymorphonuclear leukocytes. In chorioamnionitis, the levels of a variety of inflammatory modulators are increased and are thought to contribute to uterine contractions and cervical dilatation. Urinastatin has the advantage of inhibiting a variety of mediators of inflammation. In view of its broad actions, urinastatin appears well suited to inhibiting the complex array of inflammatory mediators found in chorioamnionitis. Moreover, fetal urine and amniotic fluid contain large amounts of urinastatin (Terao and Kanayama. *Sanfujinka Jissai* 37:158–68, 1988.) This suggests that the origin of the urinastatin is the fetus. Since urinastatin occurs naturally in fetuses and pregnant women, it would also appear to have the advantage of being a relatively safe drug for the fetus and pregnant woman.

The tocolytic agent may be any known tocolytic agents. The particular tocolytic agent is not critical to the invention. Beta-mimetic agents have been popular as tocolytic agents. Such beta-mimetic agents include, but are not limited to, ritodrine, terbutaline, and albuterol (salbutamol). Other tocolytic agents are believed to suppress uterine contractility by inhibiting the release of intracellular calcium, including for example, magnesium sulfate and nifedipine calcium antagonist/calcium channel blocker. Anti-prostaglandins, such as indomethacin, and have also been suggested for use as tocolytic agents but are effective for only a short time and have significant maternal and fetal toxicity.

The tocolytic agent generally is administered systemically. Although any systemic route of administration can be used, preferred routes include, but are not limited to, the intravenous and oral routes. The intravenous route may be preferred initially to develop high blood levels quickly; however, the oral route is often preferred, particularly if longer term maintenance therapy and drug administration are required.

A urinastatin-like compound includes but is not limited to urinastatin, urinastatin analogs, and urinastatin fragments. Urinastatin is a glycoprotein having an approximate molecular weight less than about 67 kD in a purified form. Urinastatin inhibits trypsin, elastase, granulocyte elastase, chymotrypsin, plasmin, hyaluronidase, amylase and creatine phosphokinase. Urinastatin has been described as inhibiting cytokine action and stabilizing lysosomal surfaces. At least a portion of the peptide urinastatin has been sequenced (EP publication No. 0 100 985, published 1 Aug. 1983).

Urinastatin-like compounds include urinastatin which has been isolated from natural sources. Natural sources include, but are not limited to, the urine of human men (as used by Mochida Pharmaceutical Co., Ltd., Tokyo, Japan). Urinastatin from natural sources may be further processed to obtain active subunits or fragments. Urinastatin may also be synthesized by either chemical or recombinant nucleic acid methods. A urinastatin-like compound can be synthesized recombinantly in homologous and heterologous cells. A urinastatin-like compound can be synthesized in $E.\ coli$ or Chinese hamster ovary (CHO) cells. Techniques for synthesis of polypeptides are described, for example, in Merrifield, $J.\ Amer.\ Chem.\ Soc.$ 85:2149–2156, 1963, incorporated herein by reference.

Analogs of urinastatin include substituted peptides which have the same active configuration as urinastatin itself. Analogs of urinastatin include polypeptides with conservative substitutions or deletions of amino acids which do not change the configuration, enzymatic activity, or activity in subject. Urinastatin analogs include glycosylated and non-glycosylated polypeptides, as well as polypeptides with other post-translational changes, such as glycosylation with different sugars, acetylation, etc.

Analogs of urinastatin also include suitable fragments, such as those portions of the protein which are effective for the intended use. Active oligopeptides include, but are not limited to, the following two peptides: an elastase inhibitor, comprising amino acids 36–50, or MGMTSRYFYN-GTSMA (SEQ ID NO:1), and an inhibitor of plasmin, trypsin and cytokines, comprising amino acids 92–106, or RAFIQLWAFDAVKGK (SEQ ID NO:2). For these relatively short oligopeptides, chemical synthesis may be preferred over recombinant synthesis.

The active oligopeptides may be administered individually or together. More preferred is their administration together. In a preferred embodiment both peptides are formulated in a vaginal suppository which also contains at least one antibiotic, preferably a cephalosporin. Another alternative is administration of one or both of the active oligopeptides conjugated to an antibiotic. One such example is the pharmaceutical conjugated compound MGMTSRYFYNGTSMA-RAFIQLWAFDAVKGK(SEQ ID NO:2)-antibiotic. Even more preferably, the antibiotic of the conjugated compound is a cephalosporin. The conjugation of the oligopeptides to the antibiotic can be performed by carboxyl and/or amide linkages using biochemical techniques well known in the art.

A urinastatin-like compound may be administered systemically or locally. More preferred is local administration. Most preferred is intravaginal administration. Vaginal administration of the urinastatin-like compound can be performed in several other ways, including douche, suppository, foam and gel forms. In the form of a douche, an aqueous solution of the urinastatin-like compound is directed against the cervix. Preferably, the urinastatin-like compounds is administered in a solid or semi-solid form (foam, gel or suppository) which retains the urinastatin at the site of administration, preferably near the cervix.

The most preferred delivery form for a urinastatin-like compound is a vaginal suppository, which is a solid dosage form varying in weight and shape. After insertion, suppositories soften, melt or dissolve in the cavity fluids. Vaginal suppositories are usually globular or oviform and generally weigh about 5 grams. The usual suppository bases are cocoa butter, glycerinated gelatin, hydrogenated vegetable oils, mixtures of polyethylene glycols of various molecular weights and fatty acid esters of polyethylene glycol. Use of cocoa butter (also known as theobroma oil or cocoa oil) is preferred. Cocoa butter melts quickly at body temperature.

Water-miscible suppository bases also may be used. Examples include polyethylene glycols or glycol-surfactant combinations. Polymers of ethylene glycol are available as polyethylene glycol polymers (Carbowax, polyglycols) of assorted molecular weights. Glycerinated gelatin is also often used as a vehicle for vaginal suppositories. Water-miscible suppository bases have the advantage of lack of dependence on a melting point approximating body temperature. Problems of handling, storage and shipping are simplified considerably.

Suppositories are prepared by well known methods including rolling (hand-shaping), molding (fusion) and cold compression.

The urinastatin-like compound is preferably administered as a single daily dose. However, the urinastatin-like compound also may be administered in two or more divided doses.

The preferred mode for preparing the urinastatin suppository is given in Example 1.

The antibiotic or combination of antibiotics contemplated in the present invention are those indicated by either diagnosis or suspected presence of microorganisms and include, for example, broad spectrum antibiotics and preferably antibiotics which are known to be effective against anaerobic bacteria. The particular antibiotic is not critical. Examples of broad spectrum antibiotics include amoxicillin, ampicillin, erythromycin, azithromycin, and cephalosporin. Clindamycin is preferred because it is effective against anaerobes. Use of more than one antibiotic, including combination antibiotics, is also contemplated in the present invention. One such combination is UNASYN® ampicillin sodium/sulbactam sodium (Roerig, Pfizer, Inc., New York, N.Y.).

An effective amount of an antibiotic is that amount normally used to treat an infection. For example, the recommended dosage of UNASYN is 1.5 to 3.0 grams every six hours. The antibiotic can be administered systemically or locally. For systemic administration, oral administration is preferred; however, other methods, such as intravenous and intramuscular administration also can be used. For local administration, the antibiotic can be inserted vaginally, in the form of a cream, suppository or other suitable dosage form.

Various regimens for administering the antibiotic(s) can be utilized. For example, mezlocillin may be given intravenously for 48 hours and followed by oral ampicillin until the delivery. Other dual antibiotic regimens comprise intravenous ampicillin/oral erythromycin and ampicillin/gentamicin. A preferred three-antibiotic regimen includes ampicillin, gentamicin and clindamycin.

The tocolytic, urinastatin-like compound and antibiotic can be administered for various period of time. In one regimen, the subject is administered an effective amount of a tocolytic agent for less than about one week, an effective amount of at least one urinastatin like compound daily until 35 weeks, and an effective amount of an antibiotic until the subject gives birth.

It is, of course, understood that the dosage, timing and administration requirements for the tocolytic agent, urinastatin-like compounds and antibiotics may differ from subject to subject and are to be determined by the person responsible for treating the subject, without undue experimentation and using techniques known within the art.

In another aspect, the above-described treatment steps are preceded by the diagnosis of impending preterm delivery. Diagnosis comprises testing for females who are at risk for preterm delivery with a method which is highly sensitive and specific for such a condition. Any suitable marker for preterm delivery can be used, so long as the test for the marker sufficiently distinguishes females at risk for preterm delivery from females who will not deliver early. A preferred test for impending preterm delivery has both specificity and sensitivity greater than about 80%. A particularly preferred method is a test for fetal fibronectin. Most preferred is an ELISA test for fetal fibronectin. An ELISA test of this type may be performed as follows.

The mucosal sample to be tested is obtained from the cervix or the posterior fornix of the vagina on a swab. The swab is placed in buffer, in which the mucosal sample is diluted. Next, the concentration of fetal fibronectin is measured with an ELISA test (Fetal Fibronectin Immunoassay, Adeza Biomedical, Sunnyvale, Calif.). This assay utilizes a monoclonal antibody specific for the oncofetal antigen, followed by a goat anti-human plasma fibronectin IgG conjugated to alkaline phosphatase and a phenolphthalein monophosphate substrate. The absorbance of each standard and sample was determined at a wavelength of 550 nm with an automated microtiter-plate reader, and fetal-fibronectin concentrations were derived from the SoftMax software program (Molecular Devices, Menlo Park, Calif.). Values greater than about 50 ng/ml, determined during weeks 21–37 of pregnancy, are significant amounts and considered predictive of impending preterm delivery.

The invention has been disclosed by direct description. The following are examples showing the efficacy of the method in diagnosing and preventing premature births in female subjects. The examples are only examples and should not be taken in any way as limiting to the scope of the method.

EXAMPLES

Example 1

Pyrogen-free urinastatin powder (Miraclid® brand) was obtained from Mochida Pharmaceutical Co., Tokyo, Japan. This powder was prepared from the fresh urine of healthy men, generally according to the method of Proksch and Routh (*J. Clin. Lab. Med.* 79:491, 1972). The dose of urinastatin was expressed in units; one unit of urinastatin inhibits 2 µg of trypsin (3200 NFU/mg, Canada Packers, Toronto, Ontario, Canada) by 50% according to the method of Kassel (*Methods Enzymol.* 19:844, 1970).

A batch of urinastatin suppositories was prepared as follows: 300,000 units of UTI powder (prepared as described above) was dissolved in 300 ml of Uretebsol W 35 sorbent for suppositories (Mochida Co., Tokyo, Japan) at 55° C. The main ingredient of Uretebsol W 35 is cocoa butter.

Next, into plastic trays with 1 ml receptacles, 1 ml aliquots of the UTI solution were poured. The trays were stored at 4° C. for about 2 hours. By then the suppositories had set, were firm and were ready to use. The completed suppositories are preferably stored at room temperature (20°–25° C.).

Example 2

168 patients in their 24th to 35 week of pregnancy were diagnosed with imminent premature delivery. The diagnosis of imminent premature delivery was based on a tocolysis index of 2 or greater. Factors of cervical dilation, ruptured membranes, uterine activity and vaginal bleeding were considered for the tocolysis index. The tocolysis index was determined by evaluating these factors and assigning points as shown in the following table. The index is the sum of these points.

| | Tocolysis Index | | | |
|---|---|---|---|---|
| | 0 pts | 1 pt | 2 pts | 3 pts |
| Cervical Dilation | 0 cm | 1 cm | 2 cm | 3 cm |
| Vaginal Bleeding | none | — | spotting | bleeding |
| Ruptured Membranes | intact | — | — | rupture |
| Uterine Activity | none | irreg. | regular | — |

A number of regimens were compared. Group 1 received ritodrine intravenous infusion at 50–300 µg per day. Groups 2 and 3 were given daily urinastatin suppositories containing 5000 units and 1000 units, respectively. Group 4 received IV ritodrine at 50–300 µg per day and one 1000 unit urinastatin suppository per day. Group 5 received IV ritodrine at 50–300 µg per day, one 1000 unit urinastatin suppository per day, and cephalosporin. The patients were treated until they delivered.

A number of parameters were tracked and are reported in FIGURE 1. The tocolysis index immediately before the start of treatment varied from 2–8. Elastase levels obtained from specimen of endocervical secretions were determined at admission to the study. "Hours to Neg UA", or the time until the number of uterine contractions in 30 minutes decreased to one or less, was reported. "Recur UA", or the proportion of women experiencing recurrence of at least one uterine contraction every 30 minutes after therapy lasting 4 days or longer was discontinued also was observed. "EGA Toco" is the estimated gestational age at the beginning of therapy. "EGA Del" is the estimated gestational age at delivery. The "interval" is the number of weeks between EGA Toco and EGA Del. "PTD<37 Wks" is the number of preterm births before 37 weeks. "PTD<34 Wks" is the number of preterm births before 34 weeks, or seriously premature infants.

All groups were comparable in maternal age, parity, estimated gestational age at start of study, tocolysis index and elastase level. However, group 5 had a relatively higher percentage of patients with tocolysis indices ≧6.

While treatment with ritodrine reduced uterine contractions more rapidly (1.4 hr compared to a study average of 3.1 hr) than other drug combinations, ritodrine alone had the highest rate of recurrence of uterine activity (over 30%) in spite of continuous administration of the drug. Finally, preterm deliveries of less than 34 and 37 wk accounted for approximately 21% and 42%, respectively, of all deliveries in women treated with ritodrine alone.

Women receiving only UTI suppositories (Group 3) experienced a slower expression of uterine activity than women receiving ritodrine, but in contrast, the recurrence rate of uterine activity was lower as was the proportion of deliveries occurring before 34 wk and 37 wk. As might be expected, combination of UTI and ritodrine rapidly suppressed uterine activity and eiminished the recurrence of uterine activity. The proportion of deliveries occurring prior to 34 and 37 wk was not diminished compared to treatment with UTI alone. The combination of UTI, ritodrine and cephalosporin successfully suppressed uterine contractility, lowered the recurrence rate of uterine activity, and unexpectedly lowered the proportion of deliveries occurring before 34 and 37 wks.

Thus, the combination of ritodrine, urinastatin and cephalosporin was surprisingly more successful than the drugs alone or the combination of ritodrine and urinastatin.

Example 3

Patients are diagnosed as having risk of imminent preterm delivery by means of the fetal fibronectin immunoassay are treated with a combination of ritodrine (a tocolytic), urinastatin (UTI) and cephalosporin antibiotic.

Mucous samples are obtained from women whose gestation period is less than about 34 weeks and who have signs and symptoms indicative of preterm delivery. The fetal fibronectin level is determined by a method which has both specificity and sensitivity greater than 80%. The mucous sample to be tested is obtained from the cervix or the posterior fornix of the vagina on a swab. The swab is placed in buffer, which dilutes the mucous sample. Next, the concentration of fetal fibronectin is measured with an ELISA test (Fetal Fibronectin Immunoassay, Adeza Biomedical). This assay utilizes a monoclonal antibody specific for the oncofetal antigen, followed by a goat anti-human plasma fibronectin IgG conjugated to alkaline phosphatase and a phenolphthalein monophosphate substrate. The absorbance of each standard and sample was determined at a wavelength of 550 nm with an automated microtiter-plate reader. Fetal-fibronectin concentrations were derived from the SoftMax software program (Molecular Devices). Patient with fetal fibronectin values greater than about 0.05 µg/ml, determined during weeks 21–37 of pregnancy, are considered to be at highest risk for impending preterm delivery (at risk of delivering within about seven days) and are entered into one of the following treatment groups.

Group A patients are given ritodrine drip infusion therapy; Group B patients are given daily UTI suppository therapy (about 1000 units/suppository); Group C patients are given a combination of daily UTI suppository and ritodrine drip infusion therapy; and Group D patients are given a combination of ritodrine infusion, UTI suppository and oral cephalosporin therapy.

After treatment, the times to depress uterine contractions are monitored after four days of therapy. After four days of therapy, treatments are stopped but UC are monitored by a belt apparatus.

Example 4

Females whose fetal fibronectin values exceed 0.05 µg/ml during weeks 21–37 of pregnancy are randomly assigned to treatment groups to receive ritodrine alone, UTI alone or combination therapy of ritodrine, UTI and antibiotic as described in Example 3. For each treatment group, patients' fetal fibronectin values before the start of therapy are plotted against the rate of premature births to determine the effect of therapy on more or less risk-prone patients.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

We claim:

1. A method of diagnosing and treating a pregnant female subject at risk for impending preterm delivery, said method comprising the steps of
   (a) testing for the presence of a significant amount of fetal fibronectin in the subject's vaginal or cervical secretions; and
   (b) if a significant amount of fetal fibronectin is present, administering to the subject the following:
      (i) a tocolytic agent;
      (ii) at least one urinastatin-like compound; and
      (iii) at least one antibiotic;
   wherein the urinastatin-like compound is selected from the group consisting of amino acids 36–50 of the urinastatin amino acid sequence, and amino acids 92–106 of the urinastatin amino acid sequence.

2. The method of claim 1 wherein amino acids 36–50 consist of MGMTSRYFYNGTSMA (SEQ ID NO:1).

3. The method of claim 1 wherein the amino acids 92–106 consist of RAFIQLWAFDAVKGK (SEQ ID NO:2).

4. The method of claim 1 wherein both MGMTSRYFYNGTSMA (SEQ ID NO:1) and RAFIQLWAFDAVKGK (SEQ ID NO:2) are administered.

5. The method of claim 1 wherein the antibiotic is selected from amoxicillin, ampicillin, erythromycin, cephalosporin, clindamycin, sulbactam sodium, and gentamicin.

6. The method of claim 1 wherein the antibiotic treatment comprises administering more than one antibiotic.

7. The method of claim 1 wherein the step of testing for fibronectin is performed by an immunoassay which is specific for the fetal form of fibronectin.

8. The method of claim 1 wherein the tocolytic agent is selected from the group consisting of ritodrine, terbutaline, albuterol, magnesium sulfate, and indomethacin.

9. A method of diagnosing and treating a pregnant female subject at risk for impending preterm delivery, said method comprising the steps of
   (a) testing for the presence of a significant amount of fetal fibronectin in the subject's vaginal or cervical secretions; and
   (b) if a significant amount of fetal fibronectin is present, administering to the subject after the diagnosis of preterm delivery is made
      (i) an effective amount of a tocolytic agent for less than about 1 week;
      (ii) an effective amount of at least one urinastatin-like compound daily selected from the group consisting of amino acids 36–50 of the urinastatin amino acid sequence, and amino acids 92–106 of the urinastatin amino acid sequence until 35 weeks after gestation; and
      (iii) an effective amount of an antibiotic until the subject gives birth.

10. The method of claim 9 wherein the tocolytic agent is selected from the group consisting of ritodrine, terbutaline, albuterol, magnesium sulfate, and indomethacin.

11. A method of diagnosing and treating a pregnant female subject at imminent risk for preterm delivery, said method comprising the steps of
    (a) testing for the concentration of elastase in the cervical and/or vaginal fluids; and
    (b) administering to the subject with an abnormally high level of elastase the following:
       (i) a tocolytic agent;
       (ii) at least one urinastatin-like compound selected from the group consisting of amino acids 36–50 of the urinastatin amino acid sequence, and amino acids 92–106 of the urinastatin amino acid sequence; and
       (iii) at least one antibiotic.

12. The method of claim 11 wherein the tocolytic agent is selected from the group consisting of ritodrine, terbutaline, albuterol, magnesium sulfate, and indomethacin.

13. A method of increasing the interval a pregnant woman carries the fetus after having been diagnosed with imminent premature delivery, said method comprising the steps of
    (a) administering an effective amount of a tocolytic agent;
    (b) administering an effective amount of at least one urinastatin-like compound selected from the group consisting of amino acids 36–50 of the urinastatin amino acid sequence, and amino acids 92–106 of the urinastatin amino acid sequence; and
    (c) administering an effective amount of at least one antibiotic.

14. The method of claim 13 wherein the tocolytic agent is selected from the group consisting of ritodrine, terbutaline, albuterol, magnesium sulfate, and indomethacin.

15. The pharmaceutical composition of the peptides MGMTSRYFYNGTSMA (SEQ ID NO:1) and RAFIQLWAFDAVKGK (SEQ ID NO:2) in combination with an antibiotic.

* * * * *